US00PP33787P2

(12) United States Plant Patent
Hokanson et al.

(10) Patent No.: US PP33,787 P2
(45) Date of Patent: Dec. 28, 2021

(54) ***RHODODENDRON* PLANT NAMED 'UMNAZ633'**

(50) Latin Name: *Rhododendron hybrida*
Varietal Denomination: UMNAZ633

(71) Applicant: Regents of the University of Minnesota, Minneapolis, MN (US)

(72) Inventors: Stanley Hokanson, North Oaks, MN (US); Steven Thomas McNamara, Victoria, MN (US)

(73) Assignee: REGENTS OF THE UNIVERSITY OF MINNESOTA, Minneapolis, MN (US)

( * ) Notice: Subject to any disclaimer, the term of this patent is extended or adjusted under 35 U.S.C. 154(b) by 0 days.

(21) Appl. No.: 17/225,284

(22) Filed: Apr. 8, 2021

Related U.S. Application Data

(60) Provisional application No. 63/101,247, filed on Apr. 21, 2020.

(51) Int. Cl.
*A01H 5/02* (2018.01)
*A01H 6/36* (2018.01)

(52) U.S. Cl.
USPC ..... Plt./240
CPC ..... *A01H 6/364* (2018.05)

(58) Field of Classification Search
USPC ..... Plt./240
CPC ..... A01H 6/364; A01H 5/02
See application file for complete search history.

*Primary Examiner* — Keith O. Robinson
(74) *Attorney, Agent, or Firm* — Penny J. Aguirre

(57) ABSTRACT

A new cultivar of hybrid *Rhododendron* plant named 'UMNAZ633' that is characterized by its rounded plant form with compactly branched plant habit; reaching 1 m in height and width after 15 years of growth, its abundance of flowers that are red in color in mid to late May in Excelsior, Minn. with the red color retained throughout the bloom period without substantial fading prior to abscission, its good cold hardiness with flower buds that are resistant to cold damage and consistently bloom even when exposed to temperatures as low as −25°, and its foliage with relatively good tolerance to powdery mildew.

2 Drawing Sheets

STATEMENT REGARDING FEDERALLY SPONSORED RESEARCH

This invention was made with government support under MN Agricultural Experiment Station (USDA/Hatch) MN 21-078, MN 21-058, and MN 22-055. The government has certain rights in the invention.

Botanical classification: *Rhododendron hybrida.*

Cultivar designation: 'UMNAZ633'.

BACKGROUND OF THE INVENTION

The present invention relates to a new and distinct cultivar of *Rhododendron* plant of hybrid origin, botanically known as *Rhododendron hybrida* 'UMNAZ633' and will be referred to hereafter by its cultivar name, 'UMNAZ633'. 'UMNAZ633' is a new cultivar of deciduous *Rhododendron* grown for use as a landscape plant.

The new cultivar was developed through an on-going breeding program conducted by the Inventors in Excelsior, Minn. The objectives of the breeding program are to develop new cultivars of *Rhododendron* that exhibit cold tolerance, excellent floral displays, disease-resistant foliage, and compact plant habits.

The new cultivar was derived from a cross made by the Inventors on May 25, 2000 between *Rhododendron hybrida* 'UMNAZ393' (not patented), as the female parent, and *Rhododendron hybrida* 'UMNAZ602' (not patented), as the male parent. The Inventors selected 'UMNAZ633' as a single unique plant amongst the seedlings that resulted from the above cross in June of 2009.

Asexual propagation of the new cultivar was first accomplished by softwood stem cuttings in Excelsior, Minn., in June of 2009 by one of the Inventors. Asexual propagation by softwood stem cuttings and tissue culture has determined that the characteristics of the new cultivar are stable and are reproduced true to type in successive generations.

SUMMARY OF THE INVENTION

The following traits have been repeatedly observed and represent the characteristics 'UMNAZ633'. These attributes in combination distinguish 'UMNAZ633' as a new and distinct cultivar of *Rhododendron.*

1. 'UMNAZ633' exhibits a rounded plant form with compactly branched plant habit; reaching 1 m in height and width after 15 years of growth.
2. 'UMNAZ633' exhibits an abundance of flowers that are red in color in mid to late May in Excelsior, Minn. with the red color retained throughout the bloom period without substantial fading prior to abscission.
3. 'UMNAZ633' exhibits good cold hardiness with flower buds that are resistant to cold damage and consistently bloom even when exposed to temperatures as low as −25° F.
4. 'UMNAZ633' exhibits foliage with relatively good tolerance to powdery mildew.

The female parent of 'UMNAZ633', 'UMNAZ393', differs from 'UMNAZ633' in having a less compact plant habit with more open branching, flowers that fade to a pale red prior to abscission, and fewer flower buds. The male parent, 'UMNAZ602', differs from 'UMNAZ633' in having flowers that are orange-red in color with an orange-gold patch on the top petal, flower buds that are less cold tolerant, and more susceptibility to powdery mildew and leaf abscission. 'UMNAZ633' can also be most closely compared to the *Rhododendron* cultivars 'Arneson Flame' (not patented) and 'UMNAZ502'. 'Arneson Flame' is similar to 'UMNAZ633' in having flowers that are red in color and a deciduous growth habit. 'Arneson Flame' differs from 'UMNAZ633' in having flower buds and stems that are less cold tolerant in U.S.D.A. Zone 4 winters. 'UMNAZ502' is similar to 'UMNAZ633' in having flowers that are red in color and flower buds that are capable of surviving temperatures of −25° F. 'UMNAZ502' differs from 'UMNAZ633' in having smaller flowers, flower buds that exhibit less red pigmentation, a larger plant size, and a less compact and less densely branched plant habit.

BRIEF DESCRIPTION OF THE DRAWINGS

The accompanying colored photographs were taken of a 17-year-old plant of the new cultivar as grown outdoors in an evaluation nursery in Excelsior, Minn.

The photograph in FIG. 1 provides a view of the overall plant habit of 'UMNAZ633' in bloom.

Figure 1:
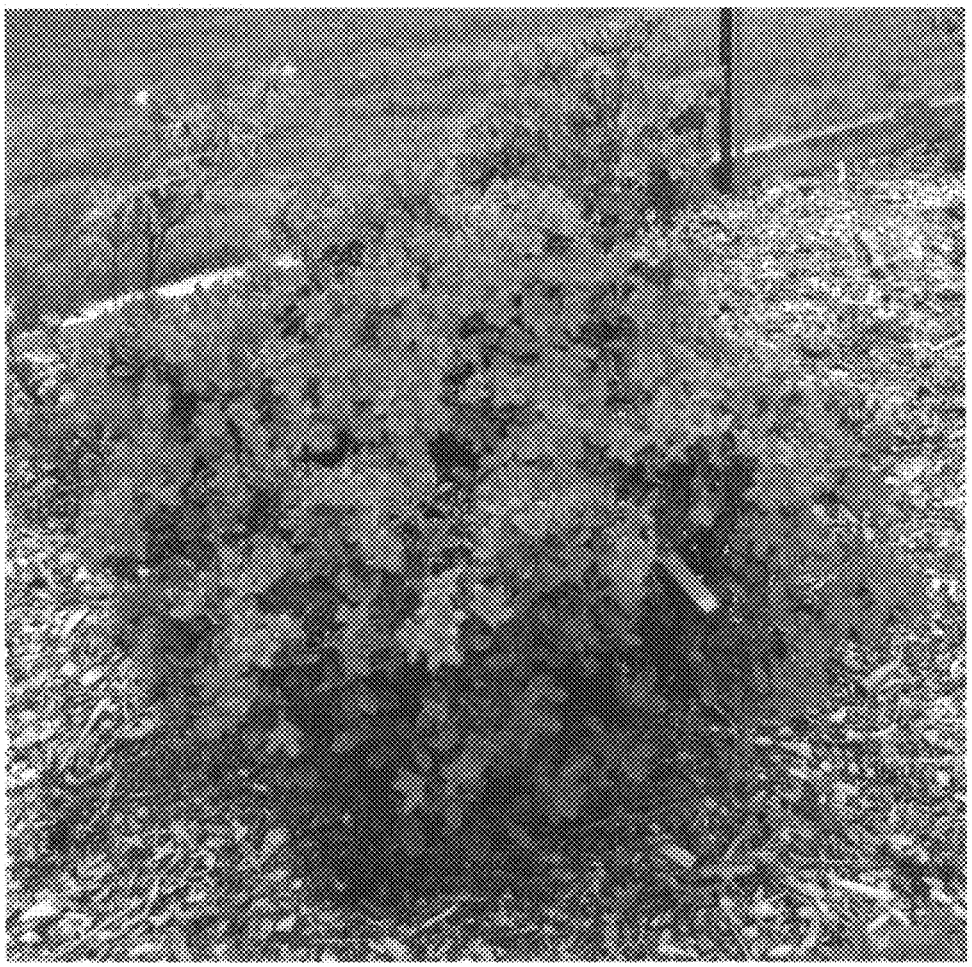
Figure 2:
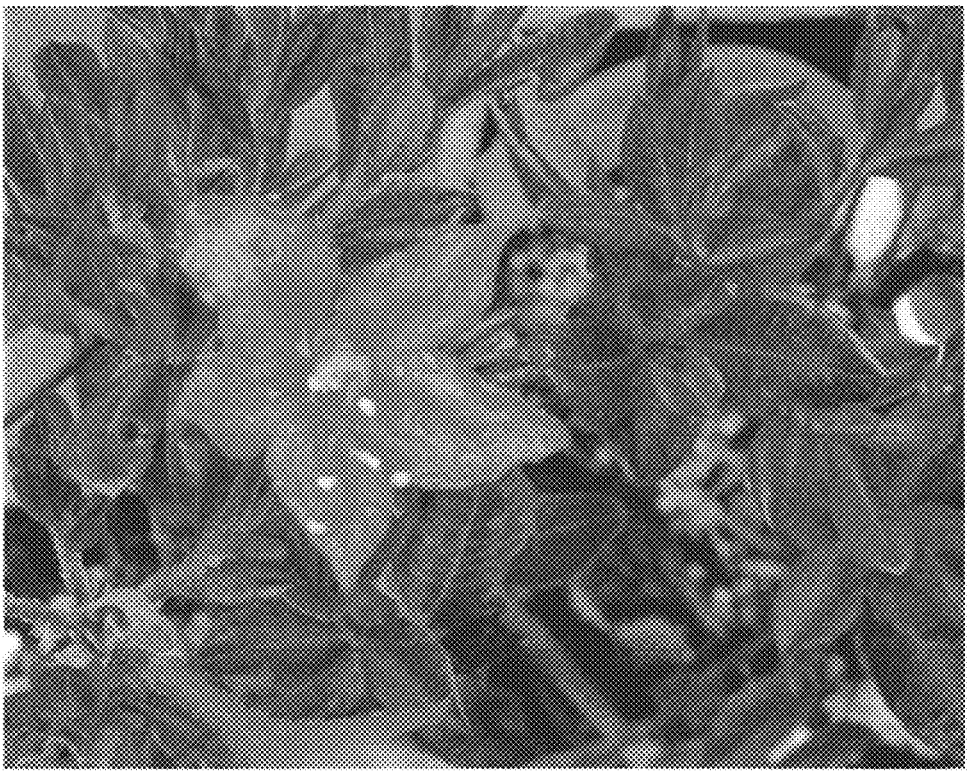

The photograph in FIG. 2 provides a close-up view of a flower and the spring foliage of 'UMNAZ633'.

Figure 3:
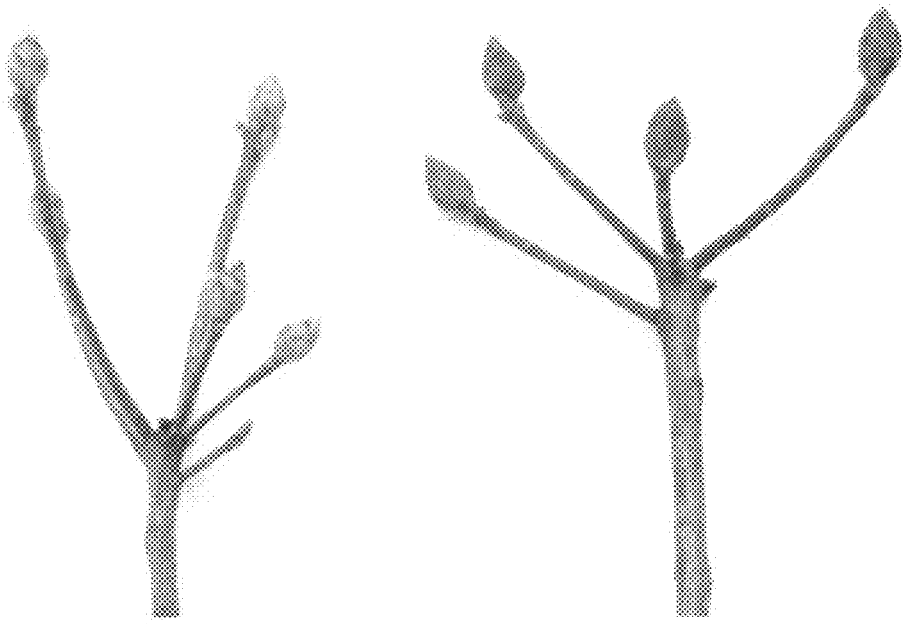

The photograph in FIG. 3 provides a close-up view of the flower buds in fall with a comparison of the flower buds of 'UMNAZ502' on the left and 'UMNAZ633' on the right.

The colors in the photographs are as close as possible with the digital photography and printing techniques utilized and the color codes in the detailed botanical description accurately describe the new *Rhododendron*.

DETAILED BOTANICAL DESCRIPTION OF THE PLANT

The following is a detailed description of 8-year-old plants of the new cultivar as grown outdoors in an evaluation nursery in Excelsior, Minn. The phenotype of the new cultivar may vary with variations in environmental, climatic, and cultural conditions, as it has not been tested under all possible environmental conditions. The color determination is in accordance with The 2015 Colour Chart of The Royal Horticultural Society, London, England, except where general color terms of ordinary dictionary significance are used.

General characteristics:

*Blooming period.*—7 to 11 days, typically commencing at the end of April in Excelsior, Minn.

*Plant type.*—Deciduous shrub.

*Plant habit.*—Rounded and densely branched.

*Height and spread.*—Reaches 1 m in height and width after 15 years in the landscape.

*Cold hardiness.*—Plant is hardy to at least U.S.D.A. Zone 4a, flower buds are resistant to cold damage when exposed to temperatures down to −25 F.

*Diseases and pests.*—Observed to have foliage that is moderately tolerant to powdery mildew (caused by *Microsphaera azalea*), no susceptibility or resistance to other diseases or insect pests has been observed.

*Root description.*—Fibrous and 165A in color.

*Propagation.*—Tissue culture (preferred) or softwood stem cuttings.

*Growth rate.*—Slow to moderate.

*Root development.*—4 to 8 weeks for root initiation and 2 years to produce a young plant from a rooted cutting.

Stem description:

*Shape.*—Round.

*Stem color.*—Young growth; 145A and 145B transitioning to N167A to 165B during growing season, mature wood; a blend of 156C and 202C.

*Stem size.*—Main stems; an average of 36 cm in length and 1 cm in width, lateral branches; an average of 17 cm in length and 5 mm in width, current year's growth; an average of 9 cm in length and 3 mm in width.

*Stem surface.*—Young growth; slightly rough to the touch, moderately covered in woolly pubescent hairs, up to 2 mm in length and 155A in color to matching stem surface, becoming smooth and glabrous in summer, mature wood; somewhat rough, dull and glabrous.

*Stem aspect.*—Held mainly vertical to slightly outward.

*Stem strength.*—Strong.

*Branching.*—Densely branched.

Foliage description:

*Leaf shape.*—Elliptic to obovate.

*Leaf division.*—Simple.

*Leaf base.*—Cuneate.

*Leaf apex.*—Acute to obtuse.

*Leaf venation.*—Pinnate, upper surface midrib 146C in color with lateral vein color matching leaf coloration, lower surface midrib and lateral veins 162A and 151A in color with short ciliate hairs on midrib that match surface color.

*Leaf margins.*—Entire and fringed with hairs; 0.5 mm in length and 155D in color.

*Leaf attachment.*—Petiolate.

*Leaf arrangement.*—Alternate, leaf clusters whorled.

*Leaf internode length.*—Ranges from 0.2 to 3.2 cm becoming progressively smaller from base to apex of shoot, 0.2 to 0.4 cm in whirl of foliage at shoot apex.

*Leaf orientation.*—Held mostly upright, some slightly downward.

*Leaf aspect.*—Whole leaf cupped upward with apex cupping downward.

*Leaf surface.*—Upper surface; smooth, glabrous, shiny with a thick texture, lower surface; smooth, dull, glabrous except prominent midrib with short cilia; <0.5 mm in length and 155B in color.

*Leaf color.*—Young leaves upper surface; 144A with transient 53A overtone in spring young leaves lower surface; a blend of 144A and 146B, mature leaves upper surface; a blend 146A and 146B, mature leaves lower surface; 147C, fall color upper surface; a blend of 46A, 147A and 166A, fall color lower surface; ranges from 144D to 183B.

*Leaf size.*—Ranging from 2.0 to 7.0 cm in length and 1.4 to 3.5 cm in width.

*Leaf quantity.*—An average of 10 leaves per lateral branch 12 cm length.

*Petioles.*—Average of 5 mm in length and 1 to 2 mm in diameter, 143B and 144A in color, smooth and lightly pubescent surface.

Flower description:

*Inflorescence type.*—Umbellate raceme.

*Lastingness of flowers.*—Individual flowers last 2 to 4 days, total duration of bloom ranges from 7 to 11 days, self-cleaning.

*Inflorescence size.*—Average of 10 cm in height and 12 cm in width.

*Flower size*.—An average of 4.5 cm in depth and 5.5 cm in diameter.

*Flower fragrance*.—Lightly fragrant.

*Flower shape*.—Broad, tubular funnel.

*Flower number*.—Average of 7 per inflorescence.

*Flower aspect*.—Outward.

*Flower bud*.—1 to 4 per terminal shoot whorl, obovate in shape, round in cross- section, pointed apex, an average of 1 cm in length and 0.6 cm in diameter, color; initially a blend of 142A and 143C in late-summer, developing 53B near the apex and margins of bud scales, especially on sun-exposed side of buds in the fall, winter buds; 166B in color with regions of 175A and 175B and some buds exhibiting 150B at base.

*Flower attachment*.—Pedicellate.

*Petal number*.—5.

*Petal shape*.—Ovate to elliptic.

*Petal color*.—Expanding flowers buds (balloon stage) are 60A in color and covered with fine hairs; 0.5 mm in length and 155D in color on lower half of the expanding corolla, upper surface color when fully open 44A and 45A, lower surface when fully open 45A and 45B often with a darker (46A) central axis.

*Petal surface*.—Upper surface; glabrous and smooth to slightly rugose, lower surface; smooth, glabrous except for moderate pubescence along the midline.

*Petal margins*.—Entire, undulate.

*Petal apex*.—Acuminate to obtuse, often recurved.

*Petal base*.—Fused.

*Petal size*.—An average of 2.7 cm in length and 1.7 cm in width.

*Sepal number*.—5.

*Sepal shape*.—Oblong to lanceolate.

*Sepal margin*.—Entire and fringed with hairs; 0.5 mm in length and 155A in color.

*Sepal size*.—Average of 3.0 mm in length and 2.5 mm in width.

*Sepal surface*.—Pubescent on upper and lower surface.

*Sepal apex*.—Obtuse to rounded.

*Sepal base*.—Fused.

*Sepal color*.—Immature upper surface; (not visible) enclosing base of the corolla tube, immature lower surface; 145A, mature upper surface; 144B and 58A near apex, mature lower surface a blend of 144A and 144B.

*Calyx*.—Shallow cup shape an average of 4.0 mm in length and 6.0 mm in diameter, with individual sepals separated by rounded sinuses.

*Pedicels*.—An average of 1 cm in length and 1.5 mm in diameter, smooth and lightly pubescent surface, 146C in color.

Reproductive organs:

*Gynoecium*.—1 Pistil, stigmas; elliptic to round in shape, 147A in color, 2 mm in diameter, style; average 7.05 cm in length, curved and 46A in color, ovary; 146C in color.

*Androecium*.—Stamens typically 5 anthers; oblong to elliptical in shape, 2 mm long and 1.5 mm wide, 164A to 164C in color; pollen 155D in color, filament; average 6.0 cm in length, curved and 44B in color.

*Fruit/seeds*.—Dehiscent, 5-valved capsule with an average of 2 cm length and 7.5 mm in width, 145B in color in late summer transitioning to 166A exterior color and 167C to 167D interior color at maturity, seed; an average of 3 mm in length and 1.5 mm in width, 164A and 166C in color, 50 to 150 seeds per capsule.

It is claimed:

1. A new and distinct cultivar of *Rhododendron* plant named 'UMNAZ633' as herein illustrated and described.

* * * * *